United States Patent [19]
Tucker et al.

[11] Patent Number: 6,074,337
[45] Date of Patent: Jun. 13, 2000

[54] COMBINATION RADIOACTIVE AND TEMPERATURE SELF-REGULATING THERMAL SEED IMPLANT FOR TREATING TUMORS

[75] Inventors: Robert D. Tucker, North Liberty; Joseph A. Paulus, Iowa City, both of Iowa

[73] Assignee: Ablation Technologies, Inc., San Diego, Calif.

[21] Appl. No.: 09/192,250

[22] Filed: Nov. 16, 1998

Related U.S. Application Data

[62] Division of application No. 08/864,486, May 28, 1997.

[51] Int. Cl.⁷ ....................................................... A61N 5/02
[52] U.S. Cl. ........................................ 600/2; 600/3; 600/4
[58] Field of Search ................................. 600/1, 2, 3, 7, 600/8, 9

[56] References Cited

U.S. PATENT DOCUMENTS

| | | |
|---|---|---|
| 4,242,089 | 12/1980 | Sasaki ..................................... 433/189 |
| 4,323,055 | 4/1982 | Kubiatowicz . |
| 4,690,130 | 9/1987 | Mirell ......................................... 600/2 |
| 4,702,228 | 10/1987 | Russell, Jr. et al. . |
| 4,784,116 | 11/1988 | Russell, Jr. et al. . |
| 4,891,165 | 1/1990 | Suthanthiran . |
| 5,084,002 | 1/1992 | Liprie . |
| 5,133,710 | 7/1992 | Carter, Jr. et al. . |
| 5,405,309 | 4/1995 | Carden, Jr. . |
| 5,429,583 | 7/1995 | Paulus et al. . |

OTHER PUBLICATIONS

"Practical Aspects of Ferromagnetic Thermoseed Hyperthermia" Brezovich, et al., pp. 589–602, Radiologic Clinics of North America, vol. 27, No. 3, May 1989.

*Primary Examiner*—Linda C. M. Dvorak
*Assistant Examiner*—B. Kearney
*Attorney, Agent, or Firm*—Nikolai, Mersereau & Dietz, P.A.

[57] ABSTRACT

An implantable seed for simultaneous delivery of thermal and radioactive radiation to target tissue comprises a tube or rod of a ferromagnetic alloy which, when subjected to an oscillating magnetic field will heat up, the alloy also being coated or otherwise treated with a radioactive isotope which gives off X-ray radiation during the decay thereof.

3 Claims, 6 Drawing Sheets

COMBINATION RADIOACTIVE AND TEMPERATURE SELF-REGULATING THERMAL SEED IMPLANT FOR TREATING TUMORS

This is a Divisional of copending application Ser. No. 08/864,486, filed on May 28, 1997.

BACKGROUND OF THE INVENTION

I. Field of the Invention

This invention relates generally to apparatus for treating malignant tumors, and more particularly to metal seeds that may be implanted by injection into tumorous tissue for allowing simultaneous application of thermal energy and radioactive emissions to such tissue.

II. Discussion of the Prior Art

In a journal article entitled "Practical Aspects of Ferromagnetic Thermoseed Hyperthermia", published in the *Radiologic Clinics of North America*, Vol. 27, No. 3, dated May 1989, Ivan A. Brezovich and Ruby F. Meredith, both with the University of Alabama at Birmingham, presented a general treatise on a method of treating tumors by interstitially implanting small pieces of ferromagnetic alloy wire into the tissue and then exposing the subject to an externally applied, oscillating, magnetic field of a predetermined frequency and field strength so as to cause inductive heating of the thermoseeds within the body. This paper points out that by selected a ferromagnetic material having a proper Curie point, such thermoseeds becomes self-regulating when the temperature of the seed approaches the Curie point at which the material becomes non-magnetic. The Carter U.S. Pat. No. 5,133,710 relates to the same technology.

The Paulus et al. U.S. Pat. No. 5,429,583, which is assigned to the assignee of the present application, describes the use of a CoPd alloy as an improved material for such thermoseeds in that by properly adjusting the percent by weight of Co and Pd in the alloy, a Curie point temperature (between 41.5° C. and 100° C.) in a therapeutic range of temperatures and an increasing magnetization with temperature characteristic until the Curie point temperature is approached is achieved upon exposure to an oscillating magnetic field. That patent and the references cited therein are hereby incorporated by reference.

It is also known in the art that particles or seeds to be implanted in tumorous tissue can be coated or otherwise treated so as to emit radiation effective in irradiating and thereby killing the tumorous tissue without excessive damage to surrounding healthy tissue. In this regard, reference is made to the Kubiatowicz U.S. Pat. No. 4,323,055, the Russell, Jr. et al. U.S. Pat. Nos. 4,702,228 and 4,784,116 and the Suthanthiran U.S. Pat. No. 4,891,165 and the Carden Jr. U.S. Pat. No. 5,405,309, each of which describes techniques for making and utilizing radioactive seed implants.

For more than a decade, medical investigators have discussed the synergy of hyperthermia and radiation in the treatment of several types of tumors. The synergism is believed to be due to some form of combined damage on a cellular level, but increasingly, investigators or theorizing that the increase in blood flow during hyperthermia facilitates the radiation dose by lowering the percentage of hypoxic cells in the tumor. It has been widely known that poorly oxygenated tumors are much more resistant to radiation than normally oxygenated cell populations. Until now, no one has disclosed a combination implant that can produce both thermal and radioactive radiations simultaneously. Thus, producing an implant which is capable of delivering truly simultaneous heat and radiation is a unique advancement, as most clinical research in this area has used separate therapies spaced as close together as possible. The present invention provides just that type of desired implant.

The combination radioactive particle emission and thermal radiation seed implant of the present invention offers the further advantage in that once the radiation levels given off by the implants have virtually disappeared, the magnetic properties of the implants remain intact, allowing for continuous hyperthermia therapy fractions at any time in the future. In normal brachytherapy seeds, after the radiation has dissipated, the implants are completely inert and have no therapeutic value whatsoever.

SUMMARY OF THE INVENTION

The present invention comprises an implantable seed for applying radioactive and thermal energy to target tissue and comprises a ferromagnetic alloy element having a shape and size permitting injection thereof into soft tissue where the element includes a radioactive material for emitting X-ray radiation upon the decay thereof, the alloy exhibiting a predetermined Curie point temperature when subjected to an oscillating magnetic field of a predetermined field strength. In accordance with a first embodiment, the ferromagnetic element may comprise a biocompatible ferromagnetic alloy or biocompatible ferrite cylindrical rod or encapsulated ferrite cylindrical rod that has been subjected to ion implantation whereby a Pd-103 or I-125 isotope is embedded below the surface of the rod.

In an alternative embodiment, the ferromagnetic alloy element may comprise a tube or rod made from ferromagnetic, such as PdCo, alloy that contains the radioactive material in the central lumen or preformed pockets therein and whose wall thickness is sufficiently thin to permit escape of X-ray particles therethrough.

The combination implant of this invention, involving both eddy-current heating with Curie temperature self-regulation and radioactive dosimetry, is specifically designed to produce a desired radiation distribution pattern for controllably applying the radiation to the target tissue without deleteriously affecting surrounding healthy tissue.

DESCRIPTION OF THE PREFERRED EMBODIMENT

The prior art references set forth in the foregoing "Discussion of the Prior Art" teach that it is necessary to encapsulate radioactive material used for radiation treatment to prevent exposure from potentially toxic nuclear decay byproducts. For example, an originally inert coating on an implant might be biocompatible radioactive gold. The nuclear decay product of Au-198, however, is mercury, hardly a biocompatible and implantable element. Hence, a combination implant, involving eddy-current heating and radioactive dosimetry, must have some form of an inert and non-radioactive encapsulation or coating to prevent potentially toxic nuclear decay products from being released into surrounding tissue or a method of implantation of the radioactive source beneath a biocompatible alloy or ferrite.

Current encapsulation designs, such as reflected in the prior art references cited herein, are not directly convertible into a useable thermoseed for several reasons. First, the space available within the seed is generally too small to contain a sufficiently large piece of low Curie temperature ferromagnetic core material to produce adequate heating power when exposed to an oscillating magnetic field to thoroughly elevate the temperature of surrounding tissue. Secondly, the length of the space within the seed is too short, such that demagnetization end effects predominate and further reduce the efficiency of the thermoseed. Thirdly, the orientation of the implant in the body tissue, which is virtually irrelevant in the case of radioactive implants, is critical in the case of ferromagnetic heating implants. To create a combination seed capable of both self-regulated heating and an adequate radiation dose about the implant, known prior art devices must be significantly modified.

Figure 1:
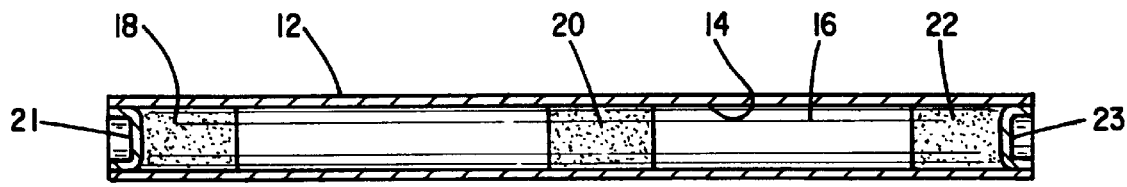
FIG. 1 illustrates a first embodiment of a combination implant constructed in accordance with the present invention.

Referring first to FIG. 1, there is shown one preferred embodiment of a combination thermal-radioactive seed implant constructed in accordance with the present invention. This implant comprises a thin-walled tube 12 of a suitable ferromagnetic alloy, such as, PdCo, that typically may be approximately 1 mm in diameter, from about 0.7 to 4 cm in length and have a wall thickness in the range of from about 0.05 to 0.1 mm. The inner lumen 14 is filled with a wire strand also made from a suitable ferromagnetic alloy or ferrite designed to exhibit the same Curie temperature as the outer alloy tube 12. The wire is identified by numeral 16 in FIG. 1 and may comprise PdCo or other, less expensive Curie point alloys, such as CuNi, FePt, or NiPd.

Predetermined segments on the wire 16 are coated or ion implanted with a radioisotope, such as Pd-103 or I-125. These segments or areas are identified by numerals 18, 20 and 22 and are shown as being shaded. The coating may be applied by any one of several processes, including, but not limited to plating, sputtering or adsorption of the radioisotope.

The wire 16 with the coated areas 18, 20 and 22 is inserted into the outer ferromagnetic alloy tube 12 so as to provide a snug fit, guaranteeing good thermal contact. This may be accomplished by cooling the core material 16 and heating the tubing 12 and then inserting the cooled wire into the heated tube. Preferably, the core material 16 should be a Curie point alloy having a similar coefficient of thermal expansion as the outer tube 12, so that it will shrink to fit into the lumen of the ferromagnetic alloy tubing, but expand and contract at the same rate as the outer tube. The radioactive core is sealed within the outer tube by end caps 21 and 23 welded in place.

By providing the radioactive material coating at opposed ends of the wire 16 and also at the middle, as at 20, the implant functions as a two or three point source rather than as a line source. This has the advantage of making the dosimetry around the implant more uniform.

The important characteristics of a radioactive implant are its half-life, its source strength and the decay particle energy of the materials employed. The half-life is the length of time required for a radioactive source to decay to one-half of its original activity. In a single half-life, one-half of the existing radioactive material undergoes a nuclear transformation by either electron capture, electron or positron emission, gamma-ray emission, or alpha particle emission, and is transformed into a more stable element. Iodine-125 exhibits a 60-day half-life, Pd-103, a 17-day half-life and Au-198, a 2.7 day half-life.

The source strength of a radioactive source is the number of radioactive events or particles given off over a specific time interval, measured in Curies. Given two samples of material with identical half-lives, where one has twice the mass of the other, the larger sample will also have a source strength twice as large.

Given two sources of equal material with different half-lives, the source with the shorter half-life will initially have a greater source strength. With time, its activity level will eventually fall below that of the other source as the amount of radioactive material in the first source will be depleted faster. Suitable radioactive implants should be capable of delivering more than 40 Gray and preferably 70 Gray over their usable life. Thus, in designing an interstitial radioactive implant, both the half-life and the source strength are important variables, where the half-life is dictated completely by the type of radioisotope, and the source strength is dependent upon both the isotope employed and the amount of radioactive material present.

The decay particle energy of the radioisotope is completely unrelated to its half-life or source strength. Typically, the decay energy originates from a specific energy event which, in turn, causes the release of specific energy X-rays. For example, Pd-103 isotopes decay by electron capture, wherein inner shell electron is adsorbed by the nucleus. The characteristic X-ray arises from an outer shell electron which jumps down to fill this vacancy. Due to small variations in the absorbed S-shell electron energy and which outer shell electron fills this vacancy, characteristic X-rays typically fall over a range rather than a single value. For Pd-103, these X-rays are 20 to 23 keV. For I-125, they are 25 to 32 keV.

Those skilled in the art will appreciate that in a clinical setting, the energy of the resulting X-rays is of particular importance, as the penetration depths of the X-rays in tissue is directly proportional to this X-ray energy. The I-125 and Pd-103 isotopes exhibit a therapeutic penetration depth in tissue of 1.0 to 1.5 cm.

Figure 2A:
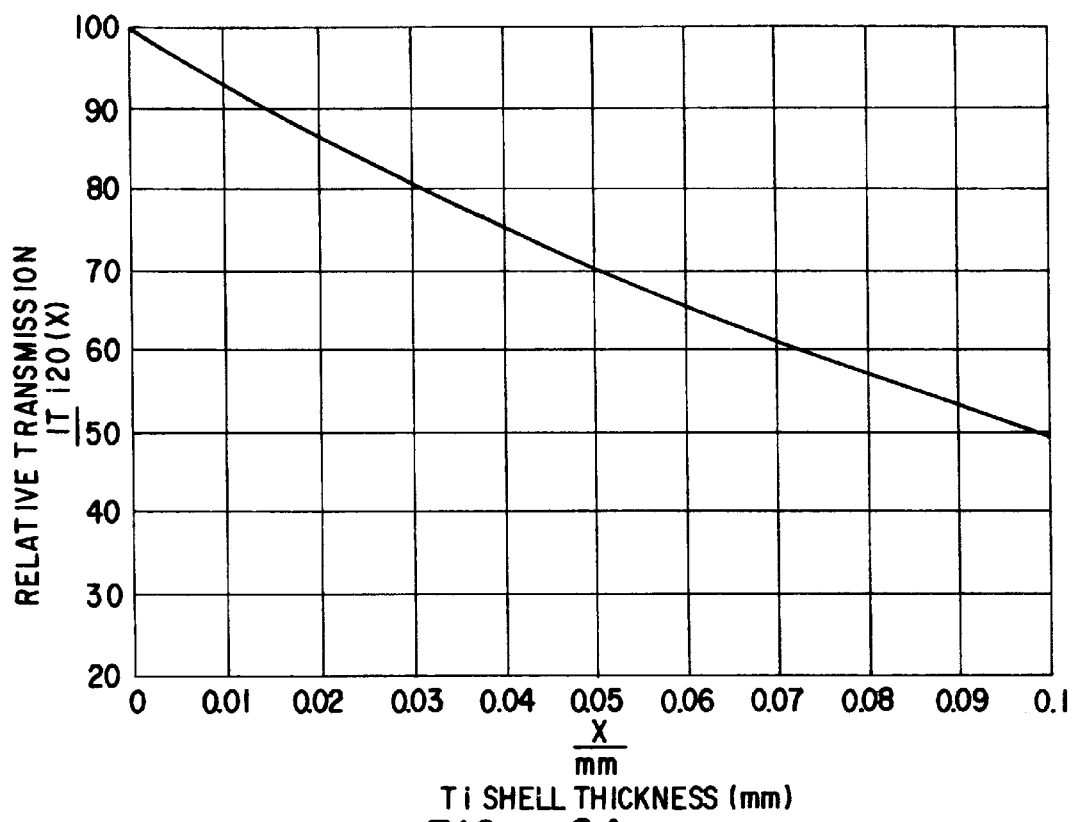
FIGS. 2A and 2B are plots of relative attenuation of X-ray emissions from Pd-103 through Ti shells of varying thickness for 20 and 23 keV energy levels, respectively.
Figure 2B:
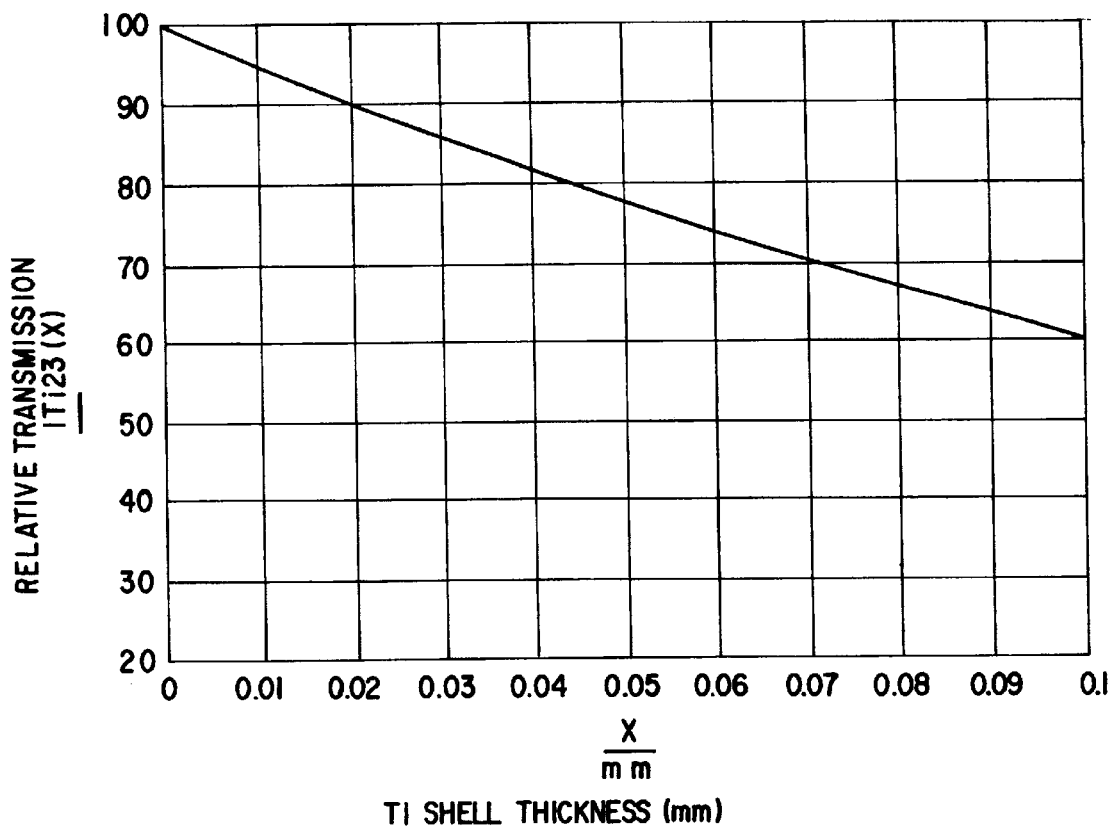
Figure 3A:
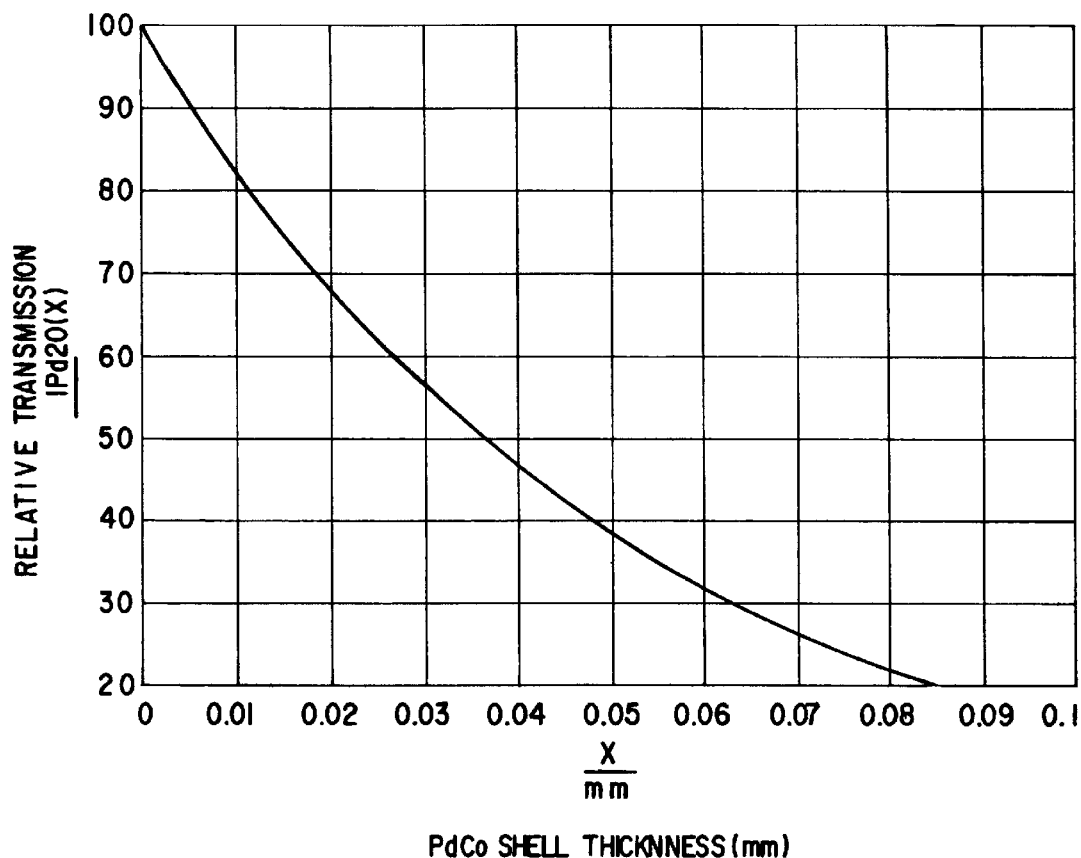
FIGS. 3A and 3B are plots similar to FIGS. 2A and 2B for PdCo alloy shells of varying thicknesses.
Figure 3B:
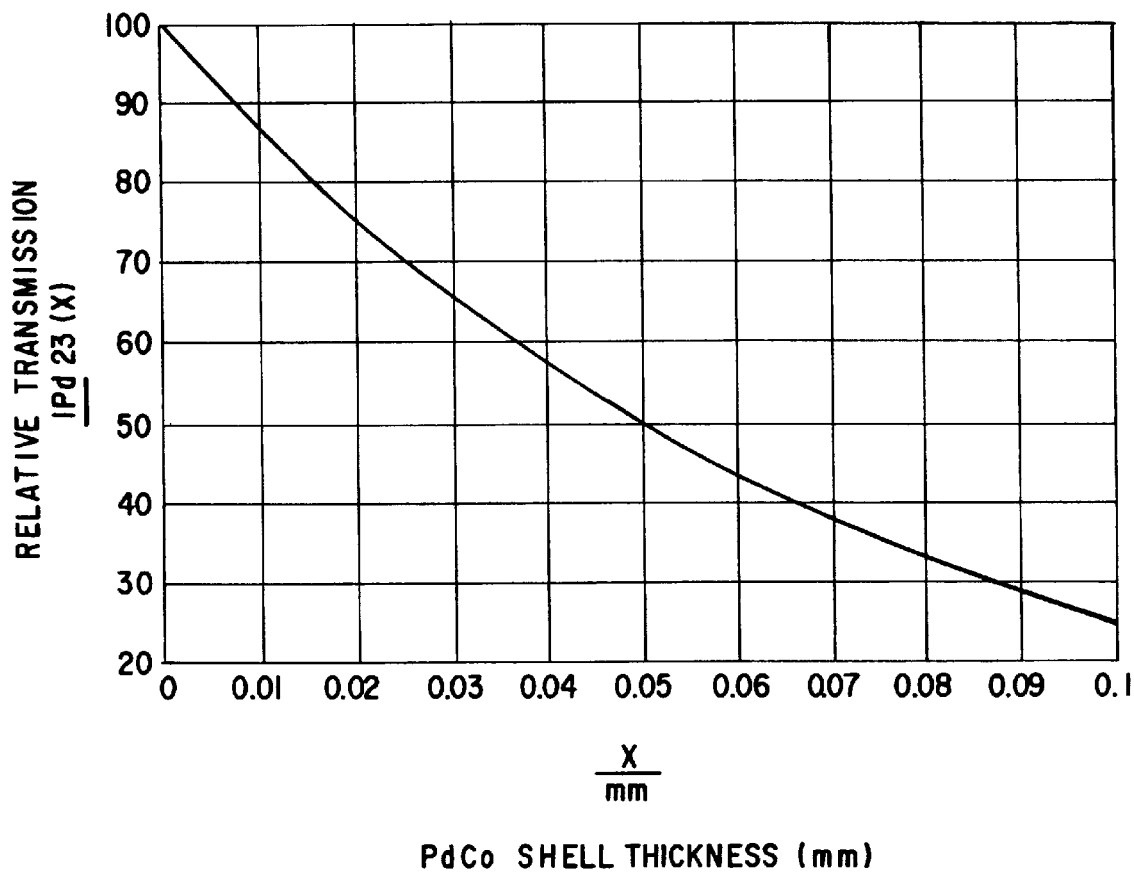

Another important aspect of the design of combination thermal and radioactive seeds is the X-ray absorption (attenuation) coefficients. X-rays traveling through a media, other than vacuum, are attenuated following statistical probabilities of an interaction with the nucleus of an atom or its surrounding electrons. In solid media, absorption or attenuation coefficients have been determined for the X-ray spectrum interactions with most common elements. The coefficients are dependent upon both the type of atom and the atomic density of the material. For Pd-103, characteristic X-rays (20–23 keV), the relative attenuation in capsules of titanium and cobalt palladium is plotted vs. wall thickness for 20 to 23 keV X-rays are illustrated in the graphs of FIGS. 2A & B and 3A & B, respectively. Each graph is normalized so that 1 equals 100% transmission. Encapsulation in Ti or PdCo tubing shields out a specific proportion of the emitted X-rays, reducing the effective source strength. Thus, thicker shell layers of more dense material are poor candidates for radioactive implant capsules. Contrarily, extremely thin shells, such as electroplated or sputtered layers have a higher probability of being damaged or breached by corrosion or possible volume changes occurring as the underlying radioisotope atoms transform into their daughter elements. We have concluded that maximum practical shell thicknesses would lie in the range of from 0.05 mm to about 0.1 mm. This would preclude the use of such otherwise biocompatible elements, such as Pt and Au, from becoming suitable candidates for the shell or capsule to be used with a combination radioactive and thermal seed implant.

The wall thickness of the PdCo tubing or coating is irrelevant from the standpoint of heating, assuming the Curie points and magnetic properties of the tubular coating and inner material are similar. Only the radioactive dosage will be varied with outer tubing thickness, as thicker tubing will block a larger portion of the emitted X-rays and require stronger internal sources to achieve adequate dosimetry.

For a PdCo tubing/coating with a ferrite core, an optimal tubing/coating thickness can be found for maximum heating efficiency. The most important factor in this configuration is the X-ray attenuation of the outer material so that the thinnest practical outer layer to insure biocompatibility and structural integrity can be used.

Figure 4:
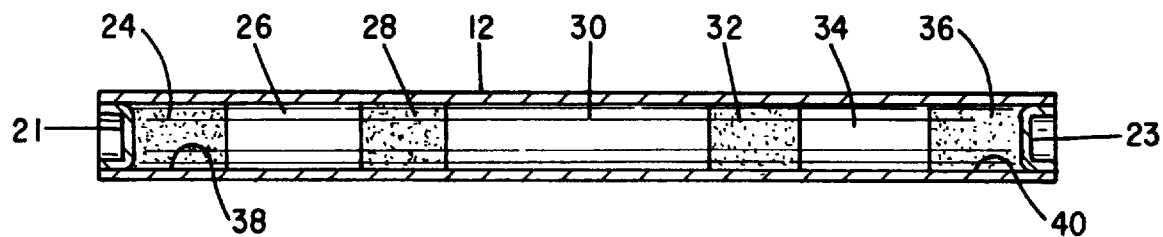
FIG. 4 is a first alternative embodiment of the combination implant.

Referring next to the combination seed implant shown in FIG. 4, this construction is substantially identical to that shown in FIG. 1, except that the inner lumen of the outer shell or tubing 12 is filled with smaller wire pieces 24–36, e.g., 1 mm to 4 mm in length, and a diameter to fit inside the 0.05 to 0.1 mm walled tubing. The individual wire or cylinder segments 24–36 are alternatively radioactive and nonradioactive, either by virtue of a coating thereon or by direct neutron irradiation. This multisource implant is designed to yield a multi-point source dosimetry. A key point with the design of FIG. 4 is that if the amount of Pd-103 daughter product (Rhodium) is small in the irradiated pieces, the Curie point and the magnetic properties of these portions may not be adversely affected. Particularly, if the radioactive pieces are also small. Using this approach, the entire implant can be manufactured out of a single alloy. It has also been found expedient to make the radioactive end sources 24 and 36 slightly larger in diameter and located in counterbores 38 and 40 formed in the opposed ends of the tube 12. The thinner wall thickness resulting from the counterbores in these areas then increases the X-ray transmission from the end sources 24 and 36 through the walls.

Figure 5:
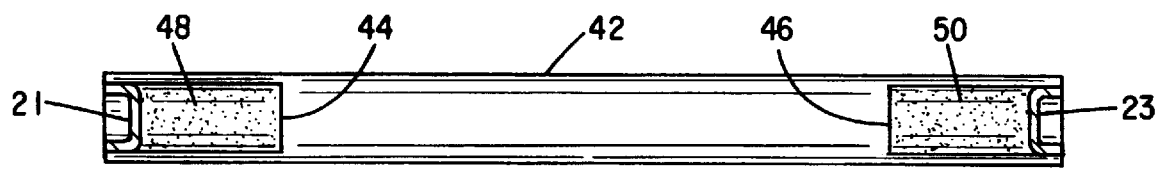
FIG. 5 illustrates yet another embodiment of a combination implant in accordance with the present invention.

With the embodiment of FIG. 5, rather than providing a tubular shell, like 12 in FIGS. 1 and 4, the implant comprises a solid rod or wire 42 of a ferromagnetic alloy, preferably PdCo. The opposed end portions of the rod 42 are drilled out as at 44 and 46 and the radioactive source material, such as Pd-103 or I-125, is packed into the cavities thus created. The rod 42 again may be at least 0.7 cm but not greater than about 4 cm in length and have a diameter of 1 mm. A preferred length is about 1.4 cm. The bores 44 and 46 are of a diameter leaving a wall thickness of about 0.05 mm surrounding the radioactive materials 48 and 50 filling the cavities. The depth of the bores may typically be up to about 4 mm in length if a Curie point alloy, such as PdCo, NiCu, NiPd or FePT with an identical Curie point is used. A Curie point ferrite could also be encapsulated in this fashion. Using a radioactive implanted or coated Curie point material in end cavities minimizes demagnetizing end effects from affecting thermal output.

Figure 6:
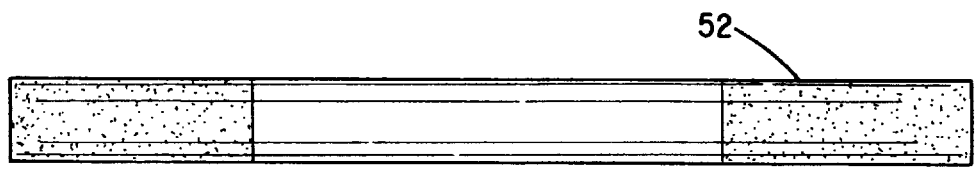
FIG. 6 depicts a further embodiment of a combination implant.
Figure 7:
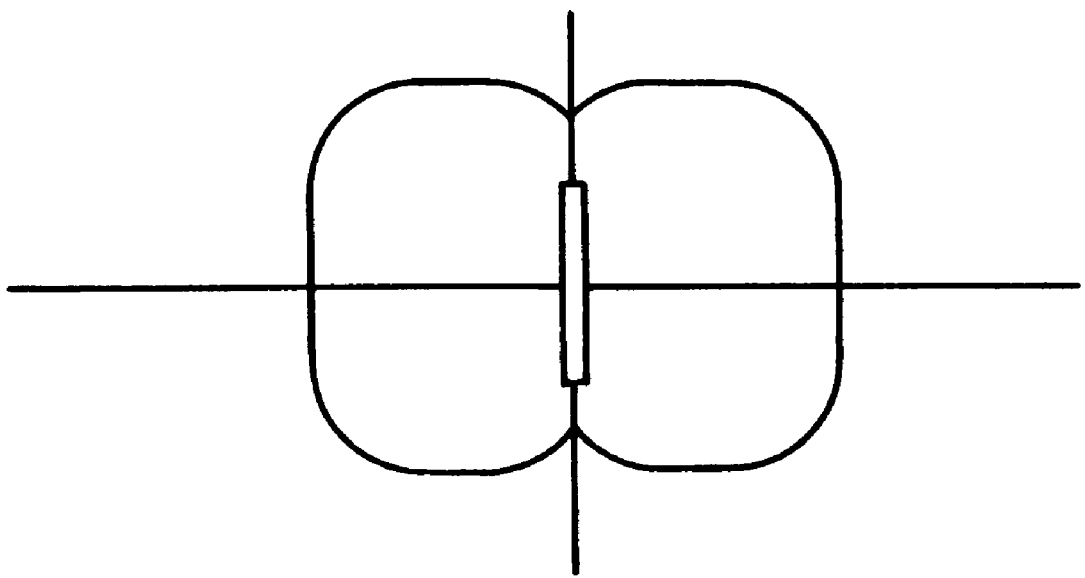
FIG. 7 illustrates a typical source dose distribution pattern for the combination implant.

The combination implant illustrated in FIG. 6 comprises a rod or wire 52 of a ferromagnetic alloy, again preferably PdCo having a percent by weight concentration of Co in a range of from about 3% to 7% with the remainder being Pd. This alloy affords the advantages explained in the aforereferenced Paulus patent. The rod 52 is subjected to ion implantation of Pd-103, either over its entire surface or in discrete zones. This process involves bombarding the surface of the rod 52 with a focused, high-energy, ion beam. The result is that the ions penetrate the surface, dissipating their energy to the atoms of the material of the rod 52 through a series of collisions. Once the ions lose all their energy, they come to rest becoming implanted in the near surface layer of the material. Conventional ion implanters used in industry accelerate the ions to energies of between 50 and 200 keV resulting in implant layer thicknesses of up to several hundred nanometers. Higher energies result in deeper penetration of the ions.

The Pd-103 decays to Rhodium which is biocompatible. Moreover, the Rhodium would be effectively buried in the PdCo rod 52 and therefore not in surface contact with adjacent tissue.

Rather than ion implanting the entire surface of the rod 52, appropriate masking techniques used during the ion implantation process can be used to concentrate the radioactive material proximate the opposed ends of the rod 52 as is illustrated in FIG. 6. By doing so, the source dose distribution provided by the seed can be tailored.

With reference again to FIG. 1, the outer tubing 12 may comprise a titanium (Ti) shell around a ferrite core 16 with a radioactive isotope, such as Pd-103 coatings selectively applied along the lengths thereof as at 18, 20 and 22. The source strengths of these sections may be made to vary to optimize dose uniformity. Rather than using a continuous ferrite core rod within a titanium tubular housing, alternate sections of ferrite with non-ferrite sources may be utilized, provided the resulting implant can generate adequate heating, given end effects of the short ferrite sections.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An implantable seed for applying radioactive and thermal energy to target tissue, comprising:

a solid, generally cylindrical rod of a PdCo alloy having a magnetic relative permeability greater than 14 and having a length and diameter permitting injection and penetration thereof into soft tissue and wherein the weight percent Pd in the alloy is in a range of from 93% to 96%, the rod including a radioactive material for emitting X-ray radiation upon the decay thereof, the alloy exhibiting a predetermined Curie point temperature in a therapeutic range between 41.5° C. and 100° C. and a power output in excess of 150 mw/cm along a longitudinal dimension thereof when subjected to an oscillating magnetic field.

2. The implantable seed as in claim 1 wherein the radioactive material has a half-life greater than 2 days and less than 100 days and a total radioactive dose in excess of 40 Gray and is ion implanted into the solid rod.

3. The implantable seed as in claim 1 wherein the solid rod includes first and second longitudinal bores extending inward from opposed ends thereof, the bores containing the radioactive material therein.

* * * * *